United States Patent
Chan et al.

(12)

(10) Patent No.: US 11,216,671 B1
(45) Date of Patent: Jan. 4, 2022

(54) ENVIRONMENT MONITORING SYSTEM

(71) Applicant: NATIONAL FORMOSA UNIVERSITY, Hu-Wei Township (TW)

(72) Inventors: Tzu-Chi Chan, Hu-Wei Township (TW); Hsin-Hsien Lin, Hu-Wei Township (TW)

(73) Assignee: NATIONAL FORMOSA UNIVERSITY, Yun-Lin County (TW)

( * ) Notice: Subject to any disclaimer, the term of this patent is extended or adjusted under 35 U.S.C. 154(b) by 0 days.

(21) Appl. No.: 17/039,325

(22) Filed: Sep. 30, 2020

(51) Int. Cl.
| | |
|---|---|
| *G01C 21/20* | (2006.01) |
| *G01K 13/00* | (2021.01) |
| *G01P 5/00* | (2006.01) |
| *G06K 9/00* | (2006.01) |
| *G01C 21/00* | (2006.01) |
| *G01N 33/00* | (2006.01) |
| *H04N 5/225* | (2006.01) |

(52) U.S. Cl.
CPC ......... *G06K 9/00791* (2013.01); *G01C 21/20* (2013.01); *G01C 21/38* (2020.08); *G01K 13/00* (2013.01); *G01N 33/0036* (2013.01); *G01P 5/00* (2013.01); *G06K 9/00255* (2013.01); *H04N 5/2253* (2013.01)

(58) Field of Classification Search
USPC .................... 348/157, 143, 144, 135, 61, 47
See application file for complete search history.

(56) References Cited

U.S. PATENT DOCUMENTS

| | | | | |
|---|---|---|---|---|
| 5,426,421 A | * | 6/1995 | Gray | .................... H04M 11/007 340/3.32 |
| 7,333,129 B2 | * | 2/2008 | Miller | .................... A62C 35/08 348/143 |
| 2015/0347827 A1 | * | 12/2015 | Dickinson | .......... G06K 9/00778 382/103 |

FOREIGN PATENT DOCUMENTS

| | | |
|---|---|---|
| CN | 204408502 U | 6/2015 |
| JP | 2003-51082 A | 2/2003 |
| TW | M537495 U | 3/2017 |

OTHER PUBLICATIONS

Taiwanese Search Report for Taiwanese Application No. 109124612, dated Mar. 19, 2021, with an English translation.

* cited by examiner

*Primary Examiner* — Daquan Zhao
(74) *Attorney, Agent, or Firm* — Birch, Stewart, Kolasch & Birch, LLP

(57) ABSTRACT

An environment monitoring system includes N sensors, a server and a monitoring device, where N≥3. The sensors respectively generate multiple pieces of sense data related to a monitoring area. The server determines whether at least three of the pieces of sense data are abnormal, and generates position data based on the at least three pieces of abnormal sense data when the determination is affirmative. The monitoring device includes a body that is movable in the monitoring area, an image capturing module and a control module. The control module controls the body to move to a position corresponding to the position data, and the image capturing module captures an image at said position.

10 Claims, 1 Drawing Sheet

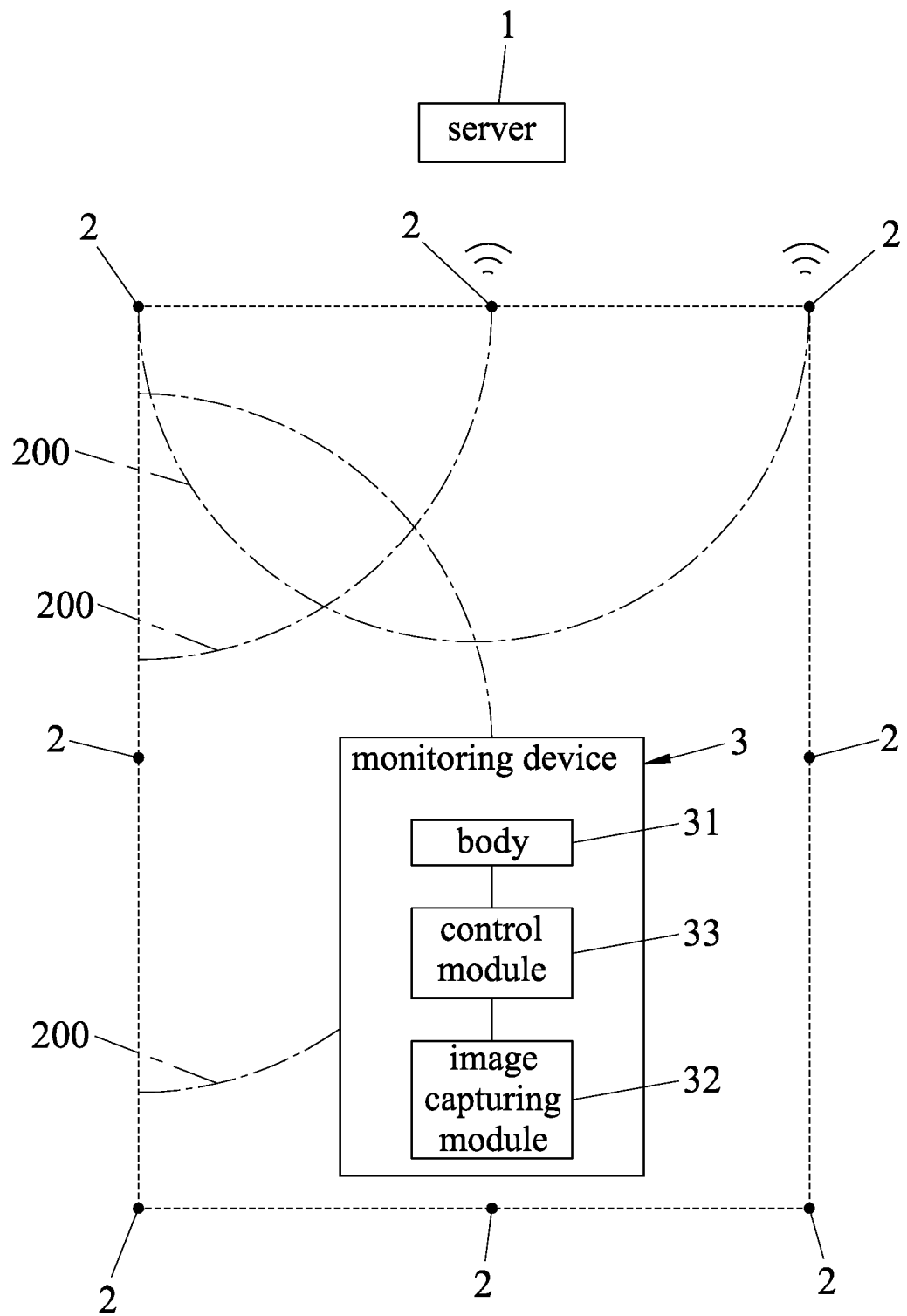

ENVIRONMENT MONITORING SYSTEM

FIELD

The disclosure relates to a monitoring system, and more particularly to an environment monitoring system for detecting abnormality in an environment.

BACKGROUND

Environmental safety has been an important issue in the industry, and it involves not only preventing and handling disasters (e.g., fire, toxic gas leakage, etc.), but also taking actions against intruders.

A conventional environment monitoring system includes a plurality of sensors that are installed in an environment to be monitored. When any one of the sensors detects abnormality in the environment, it outputs a warning signal to inform a watcher to take action against the abnormality.

Although the conventional environment monitoring system is able to output the warning signal when detecting abnormality in the environment, it has the following disadvantages. The watcher would only know which one of the sensors outputted the warning signal, but not the exact location of the abnormality. In addition, if the watcher goes straight to the environment, the watcher may put him or herself in danger (for example, toxic gas leakage, fire or attack from intruders) because the watcher lacks knowledge of the exact situation.

SUMMARY

Therefore, an object of the disclosure is to provide an environment monitoring system that can alleviate at least one drawback of the prior art.

According to the disclosure, the environment monitoring system includes a number (N) of sensors, a server and a monitoring device, where N≥3. The sensors cooperatively define a monitoring area, and respectively generate multiple pieces of sense data related to the monitoring area. The server is communicably coupled to the sensors to receive the pieces of sense data respectively therefrom, determines whether at least three of the pieces of sense data are abnormal, and generates position data based on the at least three pieces of abnormal sense data when the determination is affirmative. The monitoring device includes a body, an image capturing module and a control module. The body is movable in the monitoring area. The image capturing module is mounted to the body. The control module is disposed in the body, is communicably coupled to the server to receive the position data therefrom, is electrically coupled to the body and the image capturing module, and controls the body to move to a position that corresponds to the position data.

BRIEF DESCRIPTION OF THE DRAWING

Other features and advantages of the disclosure will become apparent in the following detailed description of the embodiment with reference to the accompanying drawing, of which:

FIG. 1 is a schematic diagram illustrating an embodiment of an environment monitoring system according to the disclosure.

DETAILED DESCRIPTION

Referring to FIG. 1, an embodiment of an environment monitoring system according to the disclosure includes a number (N) of sensors 2, a server 1 and a monitoring device 3, where N≥3. FIG. 1 depicts a scenario where N=8.

The sensors 2 are separately disposed in an environment (e.g., a factory, a park, etc.) to cooperatively define a monitoring area (e.g., an area enclosed by a dashed line as shown in FIG. 1) in the environment, and operate continuously to respectively generate multiple pieces of sense data related to the monitoring area. The monitoring area is a union of sensing ranges of the sensors 2. In particular, the sensors 2 are not arranged in a straight line (i.e., in this particular case, at least three of the sensors are arranged in a triangle arrangement), so the environment monitoring system of this embodiment can monitor a wide area. The sensors 2 are arranged in such a way that abnormality occurring at any point of the monitoring area can be detected by at least three of the sensors 2. In addition, each of the sensors 2 generates an analog signal related to the monitoring area, and converts the analog signal into a digital signal that serves as a respective one of the pieces of sense data. Moreover, each of the sensors 2 may be a temperature sensor that measures an ambient temperature, a smoke sensor that measures a concentration of suspended particles in the air, a gas sensor that detects presence of a gas in the air, or a wind sensor that measures wind speed, depending on various requirements of different environments.

The server 1 is communicably coupled to the sensors 2 to receive the pieces of sense data respectively therefrom. In addition, the server 1 stores position information (e.g., a set of coordinates) of each of the sensors 2 in the monitoring area.

During operation, the server 1 continuously receives the pieces of sense data from the sensors 2 to monitor a situation in the monitoring area. In particular, the server 1 determines whether at least three of the pieces of sense data are abnormal (referred to as at least three pieces of abnormal sense data hereinafter), and generates position data, which indicates a position of abnormality, based on the at least three pieces of abnormal sense data (e.g., the position information of those of the sensors 2 that generate the at least three pieces of abnormal sense data) when the determination is affirmative. When the determination is negative, the server 1 does not generate the position data. By generating the position data based on the at least three pieces of abnormal sense data, the position where the abnormality has occurred can be estimated more accurately.

The monitoring device 3 includes a body 31, an image capturing module 32 (e.g., a camera), and a control module 33 (e.g., a processor, a controller, etc.). The body 31 is movable in the monitoring area. The image capturing module 32 is mounted to the body 31, and is operable to capture images. In this embodiment, the monitoring device 3 is a self-propelled vehicle with photography function. The control module 33 is disposed in the body 31, is communicably coupled to the server to receive the position data therefrom, and is electrically coupled to the body 31 and the image capturing module 32. The control module 33 controls the body 31 to move to a position corresponding to the position data, controls the image capturing module 32 to capture at least one image at the position corresponding to the position data, and transmits the at least one image to the server 1.

Operations of the environment monitoring system of this embodiment will be described in detail below in a scenario where each of the sensors 2 is a temperature sensor. Each of the sensors 2 continuously measures the ambient temperature to generate the respective one of the pieces of sense data in digital form. The server 1 continuously receives the pieces of sense data from the sensors 2 to monitor a temperature condition of the monitoring area.

When determining that the temperatures indicated by at least three of the pieces of sense data are greater than a predetermined threshold (i.e., the at least three of the pieces of sense data are abnormal), the server obtains at least three possible ranges 200 respectively based on the at least three pieces of abnormal sense data, and generates the position data based on an intersection of the possible ranges 200. Each of the possible ranges 200 falls within the sensing range of the sensor 2 generating the corresponding piece of abnormal sense data. In an example, each of the possible ranges 200 is in the shape of a circular sector that has a central angle of 90° or 180°, that has a vertex (i.e., a center of a circle from which the circular sector is cut) where the sensor 2 generating the corresponding piece of abnormal sense data is located, and that has a radius (of the circle from which the circular sector is cut) inversely proportional to deviation of the temperature indicated by the corresponding piece of abnormal sense data from the predetermined threshold. When determining that the possible ranges 200 intersect at a point, the server 1 takes a set of coordinates of the point as the position data, and transmits the position data to the control module 33. When determining that the possible ranges 200 have an intersection but the intersection is not a point, the server 1 calculates an average of multiple sets of coordinates of multiple points along a boundary of the intersection (mutually overlapping area of the possible ranges 200) to serve as the position data, and transmits the position data to the control module 33. The server 1 further informs a watcher (e.g., monitoring personnel, a guard, etc.) of the position data (e.g., by displaying text or outputting sound), so the watcher can know the position of the abnormality. When determining that the possible ranges 200 do not intersect (no mutually overlapping point or area among all the possible ranges 200), the server 1 does not generate the position data. In response to receipt of the position data, the control module 33 controls the body 31 to move to the position corresponding to the position data, controls the image capturing module 32 to capture at least one image at the position corresponding to the position data, and transmits the at least one image to the server 1. In response to receipt of the at least one image, the server 1 displays the at least one image to inform the watcher of the situation at the position corresponding to the position data, so the watcher can take proper actions. This reduces the risk of danger resulting from the watcher going straight to the position of the abnormality without any knowledge of the situation.

In this embodiment, the server 1 includes a face recognition model. In response to the receipt of the at least one image, the server 1 uses the face recognition model to determine whether an intruder appears in the at least one image. In particular, the server 1 stores multiple pieces of face data of persons who are allowed to enter the monitoring area (e.g., employees of a factory). In response to the receipt of the at least one image, the server 1 uses the face recognition model to determine whether a human face appears in the at least one image and whether the human face, if any, matches one of the pieces of face data. When it is determined that a human face appears in the at least one image and that the human face does not match any one of the pieces of face data, the server 1 determines that an intruder has entered the monitoring area, and informs the watcher of this determination (e.g., by outputting light or sound), so the watcher can take proper actions.

In this embodiment, the control module 33 stores a map of the monitoring area. In response to the receipt of the position data, the control module 33 determines, based on the map and the position data, a route (e.g., a fastest route or a best route) from a position of the body 31 to the position corresponding to the position data, and controls the body 31 to follow the route to move to the position corresponding to the position data.

In some embodiments, the server 1 may generate the position data when determining that three of the possible ranges 200 intersect. Moreover, in some embodiments, in a case where the server 1 obtains more than three possible ranges 200, the server 1 may generate the position data when determining that all of the possible ranges 200 intersect.

In application, there may be multiple monitoring areas in the environment. In the case where there are multiple monitoring areas in the environment, each of the monitoring areas is defined by corresponding sensors 2, so independent incidents of abnormality can by monitored simultaneously.

In view of the above, the environment monitoring system of this disclosure has the following advantages.

1. Since the server 1 can obtain the position data based on the at least three pieces of abnormal sense data, the watcher can know the position where the abnormality has occurred.

2. Since the monitoring device 3 can move to the position corresponding to the position data, capture at least one image at the position corresponding to the position data, and transmit the at least one image to the server 1, and since the server 1 can display the at least one image for view by the watcher, the watcher is able to learn about the situation at the position of the abnormality, thereby reducing the risk of danger that results from the watcher directly going to the position of the abnormality without being prepared. In addition, the watcher can take action in a timely fashion to limit damage caused by the abnormality.

In the description above, for the purposes of explanation, numerous specific details have been set forth in order to provide a thorough understanding of the embodiment. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what is considered the exemplary embodiment, it is understood that the disclosure is not limited to the disclosed embodiment but is intended to cover various arrangements included within the spirit and scope of the broadest interpretation so as to encompass all such modifications and equivalent arrangements.

What is claimed is:

1. An environment monitoring system comprising:
   a number (N) of sensors cooperatively defining a monitoring area, and respectively generating multiple pieces of sense data related to the monitoring area, where N≥3;
   a server communicably coupled to said sensors to receive the pieces of sense data respectively therefrom, determining whether at least three of the pieces of sense data are abnormal, and generating position data based on the at least three of the pieces of sense data when the determination is affirmative; and a monitoring device including
a body movable in the monitoring area,
an image capturing module mounted to said body, and
a control module disposed in said body, communicably coupled to said server to receive the position data therefrom, electrically coupled to said body and said image capturing module, and controlling said body to move to a position that corresponds to the position data.

2. The environment monitoring system of claim 1, wherein said sensors are not arranged in a straight line.

3. The environment monitoring system of claim 1, wherein, when the determination is affirmative, said server obtains at least three possible ranges respectively based on the at least three of the pieces of sense data, and generates the position data based on an intersection of the at least three possible ranges.

4. The environment monitoring system of claim 3, wherein:
when the intersection of the at least three possible ranges is a point, said server takes a set of coordinates of the point as the position data; and
when the intersection of the at least three possible ranges is not a point, said server calculates an average of multiple sets of coordinates of multiple points on a boundary of the intersection to serve as the position data.

5. The environment monitoring system of claim 1, wherein each of said sensors generates an analog signal related to the monitoring area, and converts the analog signal into a digital signal that serves as a respective one of the pieces of sense data.

6. The environment monitoring system of claim 1, wherein:
said control module controls said image capturing module to capture at least one image at the position corresponding to the position data, and transmits the at least one image to said server;
said server includes a face recognition model; and
in response to receipt of the at least one image, said server uses the face recognition model to determine whether an intruder appears in the at least one image.

7. The environment monitoring system of claim 1, wherein said control module stores a map of the monitoring area, determines, based on the map and the position data, a route from a position of said body to the position corresponding to the position data, and controls said body to follow the route to move to the position corresponding to the position data.

8. The environment monitoring system of claim 1, wherein said sensors include at least one of a temperature sensor, a smoke sensor, a wind sensor or a gas sensor.

9. The environment monitoring system of claim 1, wherein, when the determination is affirmative, said server obtains at least three possible ranges respectively based on the at least three of the pieces of sense data, and generates the position data based on an intersection of three of the at least three possible ranges.

10. The environment monitoring system of claim 9, wherein:
when the intersection of the three of the at least three possible ranges is a point, said server takes a set of coordinates of the point as the position data; and
when the intersection of the three of the at least three possible ranges is not a point, said server calculates an average of multiple sets of coordinates of multiple points on a boundary of the intersection to serve as the position data.

* * * * *